(12) United States Patent
Reinisch et al.

(10) Patent No.: US 8,711,354 B2
(45) Date of Patent: Apr. 29, 2014

(54) METHOD FOR SPORE DETECTION

(75) Inventors: Lou Reinisch, Christchurch (NZ); Steven Churchwell, Christchurch (NZ)

(73) Assignee: Veritide Limited, Llam, Christchurch (NZ)

(*) Notice: Subject to any disclaimer, the term of this patent is extended or adjusted under 35 U.S.C. 154(b) by 0 days.

(21) Appl. No.: 13/404,396

(22) Filed: Feb. 24, 2012

(65) Prior Publication Data

US 2013/0169952 A1 Jul. 4, 2013

Related U.S. Application Data

(63) Continuation of application No. 12/129,931, filed on May 30, 2008, now abandoned.

(60) Provisional application No. 60/941,084, filed on May 31, 2007.

(51) Int. Cl.
*G01J 4/00* (2006.01)
*G01J 3/00* (2006.01)
*G01N 21/64* (2006.01)

(52) U.S. Cl.
USPC .......................... 356/369; 356/51; 250/461.2

(58) Field of Classification Search
USPC ......... 356/128, 337, 338, 369, 432, 433, 434, 356/436, 437, 438, 439, 441, 51; 250/458.1, 461.1, 461.2
See application file for complete search history.

(56) References Cited

U.S. PATENT DOCUMENTS 6,337,739 B1* 1/2002 Koelblin et al. ............... 356/336
2006/0292664 A1* 12/2006 Ponce .............................. 435/34

FOREIGN PATENT DOCUMENTS

| EP | 1329514 A2 * | 7/2003 |
| WO | WO 03024491 A2 * | 3/2003 |
| WO | WO 2004015136 A1 * | 2/2004 |
| WO | WO 2005090975 A1 * | 9/2005 |
| WO | WO 2006091223 A2 * | 8/2006 |

OTHER PUBLICATIONS

Bronk, B.V. et al. "Physical Perturbation for Fluorescent Characterization of Microorganism Particles". In: Chemical and Biological Sensing, Edited by P.J. Gardner, Proc. SPIE, 2000, vol. 4036, pp. 169-180.*

* cited by examiner

*Primary Examiner* — Michael A Lyons
(74) *Attorney, Agent, or Firm* — Dann, Dorfman, Herrell and Skillman, P.C.

(57) ABSTRACT

A method of detecting the presence of bacterial spores in a sample comprises non-destructively to the spores carrying out the steps of assessing the absorption, reflectance, and/or index of refraction (IOR) of the sample, subjecting the sample to UV radiation, and reassessing the absorption, reflectance, and/or index of refraction (IOR) of the sample to determine the presence or absence of spores. A detector is also disclosed.

10 Claims, 10 Drawing Sheets

METHOD FOR SPORE DETECTION

REFERENCE TO PRIOR APPLICATION

This application is a continuation of U.S. Application Ser. No. 12/129,931, filed May 30, 2008, now abandoned, which claims the benefit of U.S. Provisional Application No. 60/941,084, filed May 31, 2007.

FIELD

The present invention relates to a system for the detection of bacterial spores.

BACKGROUND

Systems for the detection of chemical and biological weaponry are of increasing international interest. A biological weapon incorporates an organism (bacteria, virus or other disease-causing organism) or toxin found in nature as a weapon of war. Biological warfare agents of critical concern include bacterial spores such as *Bacillus anthracis* (anthrax), *Clostridium tetani* (tetanus), and *Clostridium Botulinum* (botulism). Particularly *Bacillus* bacteria and *Clostridium* bacteria form bacterial spores.

Dipicolinic acid (pyridine 2,6 dicarboxylic acid) (DPA) is a major component of bacterial spores and it is unique in that it has only been found in bacterial spores. Up to 15% of a spore's dry weight may consist of DPA complexed with calcium ions (CaDPA).

OBJECT OF THE INVENTION

It is an object of the present invention to provide a system for the detection of bacterial spores.

SUMMARY OF THE INVENTION

In one aspect of the invention there is provided a method for detecting bacterial spores in a sample comprising the steps of assessing the absorption, reflectance, and/or Index of Refraction (IOR) of the sample, subjecting the sample to UV radiation, and reassessing the absorption, reflectance, and/or IOR of the sample to detect for the presence of spores.

The absorption, reflection and IOR assessment and/or re-assessment after exposure to the short-wave UV irradiation can be carried out on the intact spore, or after destroying the spore with heat or ultrasonication or chemical means to break open the spore for the purpose of extracting the DPA.

The method utilises an initial assessment of the absorption, reflectance, and/or IOR of the sample followed by irradiation with UV radiation and then a reassessment of the absorption, reflectance, or IOR of the sample to detect an increase in reflection, a decrease in absorption, or changes in IOR between the two assessments. Such absorption, reflectance, and/or IOR changes are indicative of the presence of spores. The actual absorption, reflectance, and/or IOR, or simply a change in absorption, reflectance, and/or IOR between the two measurements, may be determined.

Optimal wavelengths for effecting the changes in absorption, reflection, and/or IOR are generally in the range 200 to 300 nm, for the UV exposure between the assessment and reassessment of absorption, reflectance, and/or IOR. The exposure time for optimal effect depends upon the intensity of the UV radiation source and the number of spores that may be present in the sample. Preferably the exposure time is less than 10 minutes, and most preferably less than 5 minutes.

In one embodiment the sample may be immobilised on a support and the step of subjecting the sample to UV radiation occurs by irradiating the sample on the support with UV radiation.

In an alternative embodiment the sample may be airborne and the step of subjecting the sample to UV radiation occurs by causing the sample to pass through a beam of UV radiation.

In an alternative embodiment the sample may be a solution or a suspension, and the solution or suspension may be irradiated.

In another aspect of the invention there is provided a detector for detecting bacterial spores in a sample comprising a UV source, a detection zone within which the sample may be placed or may pass, means for absorption, reflectance, and/or IOR analysis arranged to assess for the presence of spores by reference to a change in absorption, reflectance, and/or IOR following exposure of the sample to a UV source between assessments with or without altering the structure of any spore.

The detector is arranged to make an initial measurement of the absorption, reflectance, and/or IOR of the sample, followed by irradiation with UV radiation and then a re-measurement of the absorption, reflectance, and/or IOR of the sample. The results of the measurements may be output as actual absorption, reflectance, and/or IOR measurements, or as a reading of the change in absorption, reflectance, and/or IOR between the two measurements.

Preferably the irradiating source designed to effect the changes in absorption, reflectance and/or IOR is arranged to subject the sample to UV radiation of wavelength in the range 200 to 300 nm.

In another aspect of the invention there is provided a method of detecting bacterial spores in a sample comprising the steps of providing a detector as described above, positioning the detector so that the sample is in the detection zone, and analysing the spore content of the sample, wherein the step of analysis of the spore content includes measuring the absorption, reflectance, and/or IOR of the sample; exposing the sample to UV radiation and then re-measuring the absorption, reflectance, and/or IOR of the sample wherein the structure of any spore remains unaltered throughout the steps of the method.

In another aspect of the invention there is provided a method of ascertaining whether a sample, due to its content of bacterial spores, presents a threat to a mammal comprising the steps of providing a detector as described above, setting the sensitivity of the detector at a predetermined threshold above which a threat would be considered to be present, positioning the detector so that the sample is in the detection zone, reading or interpreting the output of the detector as either:

a. beyond the threshold and thus the sample presents a threat, or b. under the threshold and thus the sample does not present a threat, wherein the structure of any spore remains unaltered throughout the steps of the method.

Bacterial spores which may be detected by the invention include spores of *Bacillus anthracis, Clostridium tetani*, and *Clostridium botulinum*.

The threat may be of biological warfare. Alternatively the threat may be of bacterial contamination of a material. For example the material may be a foodstuff such as flour or milk powder and bacterial spores may include *Bacillus* spores.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

DEFINITIONS

As used herein the following terms have the meanings given:

"bacterial spore" means an endospore produced within a bacterium.

"absorption" is used interchangeably herein with absorbance and both mean the absorption of light by a sample, from an external source. This is also the imaginary part of the complex refractive index of a material.

"reflectance" means the reflection of light by a sample, from an external source.

"absorption, reflectance, and/or IOR" means absorption, reflectance, and/or Index of Refraction, or any combination of these.

"Index of Refraction" means the ratio of the phase velocity of light in vacuum to the velocity of light in the medium itself. This is also the real part of the complex refractive index of a material.

"sample" means any sample of whatever form including particulate, on a surface or airborne, in solution or suspension including cloudy liquids such as milk.

"support" means some form of substrate, slide or other surface upon which the sample may be immobilised even if only temporarily.

"and/or" means "and" or "or", or both.

As used herein "(s)" following a noun means the plural and/or singular forms of the noun.

The term "comprising" as used in this specification and claims means "consisting at least in part of", that is to say when interpreting independent paragraphs including that term, the features prefaced by that term in each paragraph will need to be present but other features can also be present.

BRIEF DESCRIPTION OF THE DRAWINGS

The invention will now be described by way of example only and with reference to the drawings in which.

DETAILED DESCRIPTION OF THE INVENTION

We have found that DPA and CaDPA in spores will exhibit absorption, reflectance, and/or IOR changes upon UV exposure with or without first requiring breakdown of the spore structure, by heating in water for example, to release the DPA/CaDPA into the supernatant liquid. The invention comprises:

assessing the absorption, reflectance, and/or IOR of a sample (such as but not limited to dust, powder or a solution) which is suspected of containing bacterial spores, exposing the sample to ultraviolet radiation, reassessing the absorption, reflectance, and/or IOR of the sample, and determining the presence (or absence) of spores.

Figure 1:
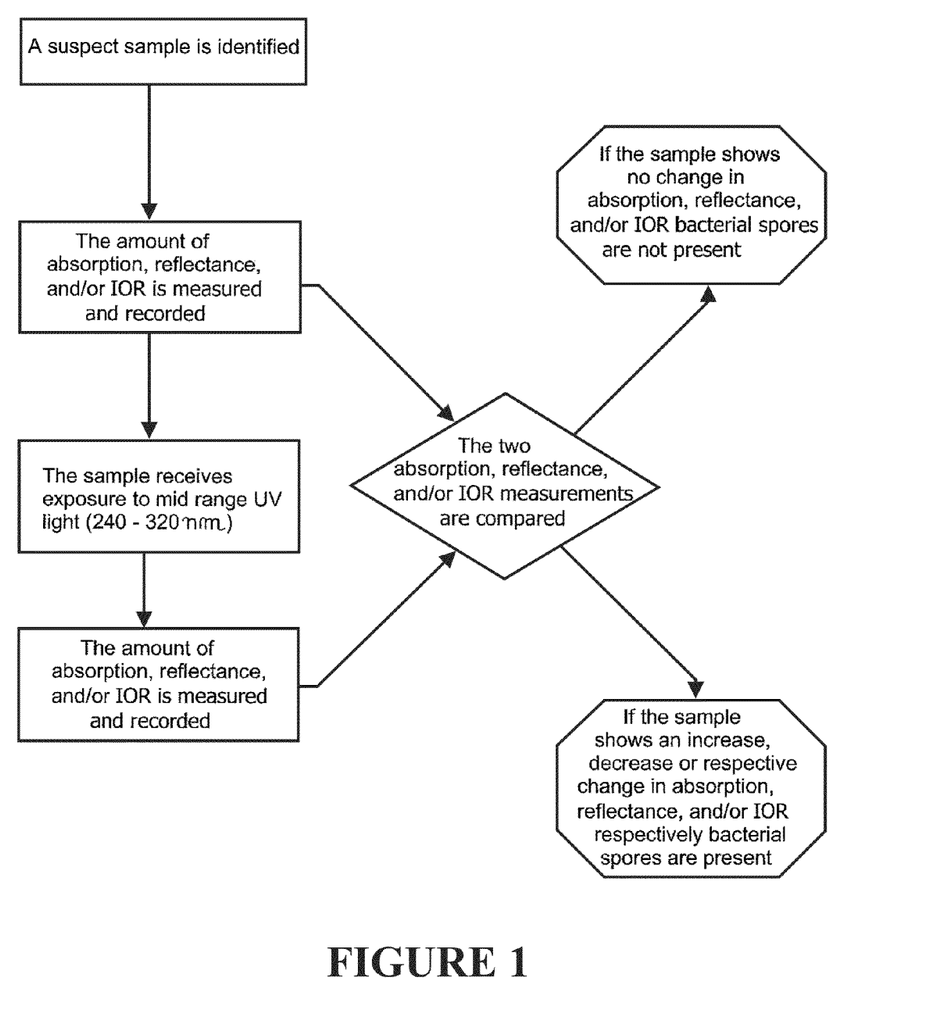
FIG. 1: is a generalised flow diagram of the method of the invention.

If the absorption, reflectance, and/or IOR is altered appropriately after exposure to UV radiation the sample is assessed as containing bacterial spores. The method is illustrated generally in the flow diagram of FIG. 1 (in which the wavelength ranges are given by way of example).

It should be noted that absorption, reflectance and IOR are related quantities. In particular the IOR can be determined from the absorption through the Kramers-Kronig relations. The absorption coefficient of a material is the imaginary part of the complex quantity called the refractive index of the material. The IOR is the real part of the complex quantity called the refractive index of the material. The Kramers-Kronig relations allows one to find the real part from the imaginary part and the imaginary part from the real part. Thus, the index of refraction is linked to the absorption in a well-known relation. Therefore changes in the photochemical properties of the samples can be determined by detecting changes in the absorption, reflectance, and/or IOR separately, or in any combination.

Figure 2:
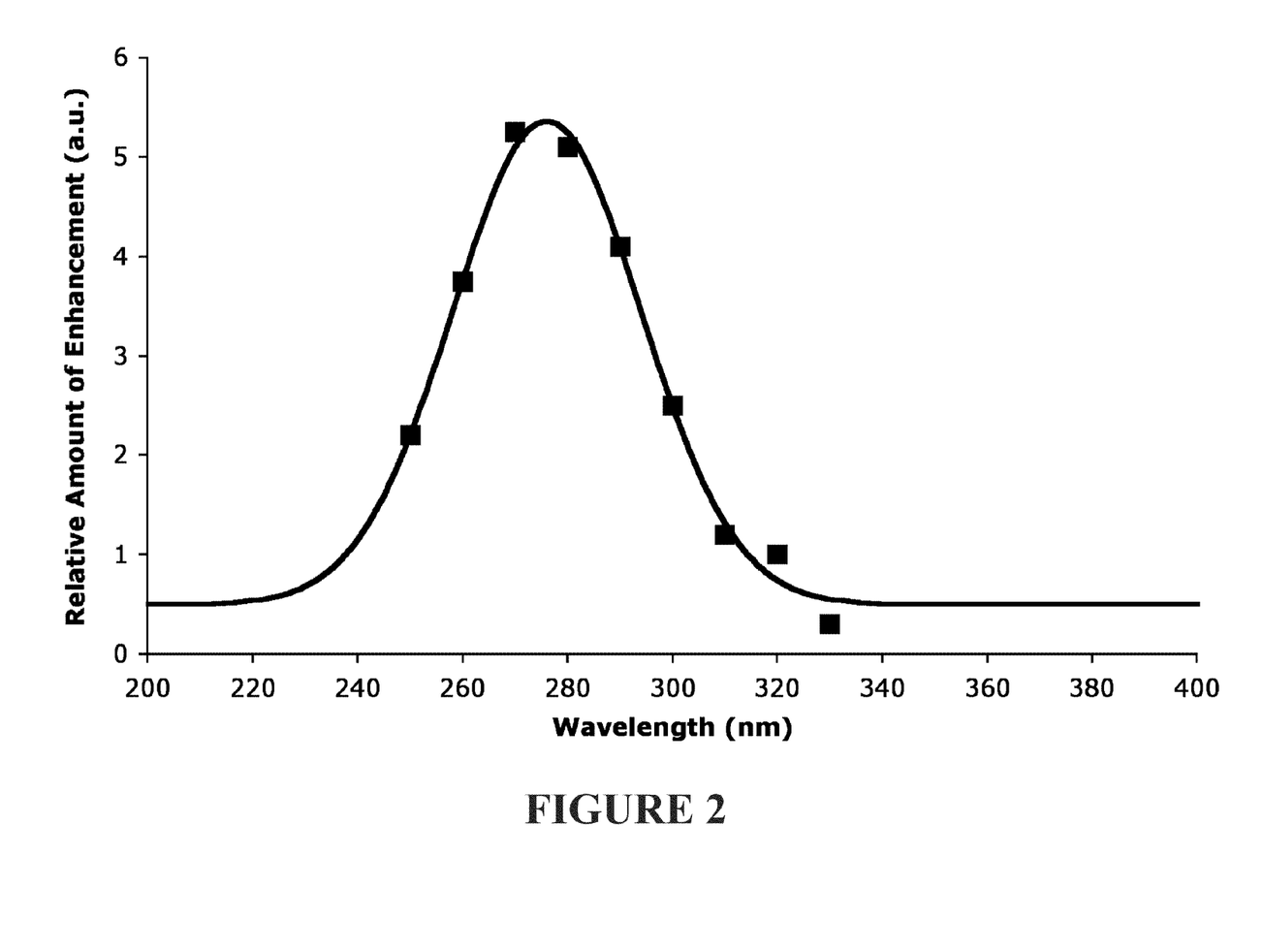
FIG. 2: is a plot of the spectral response for the changes of the DPA absorption, reflectance, and/or IOR.

FIG. 2 shows the spectral response curve for the effective change of the DPA absorption, reflectance, and/or IOR. The full range of effective change runs from about 230 nm to 330 nm. The squares show measured intensities. The line is a least squares fit of a Gaussian profile to the measured data. As the maximum change is observed at or near 280 nm this is an ideal region of the spectrum for assessing absorption, reflectance, and/or IOR changes.

In the assessment and reassessment of absorption, reflectance, and/or IOR the sample is preferably exposed to UV-visible in the wavelength range 300-600 nm.

The invention provides a method for detection of spores which can be carried out non-destructively with or without requiring heating of spores in a wet environment. Thus the method may be implemented, for example, on a desktop, or an envelope by a handheld detector, via a detector incorporated in a roller in a mail sorting machine, or for airborne spores.

Operational modes may include continuously blowing an air sample through a detector or taking a sample of a suspect powder by picking it up on tape or using an electrostatic screen or taking a sample of a liquid specimen.

Figure 3:
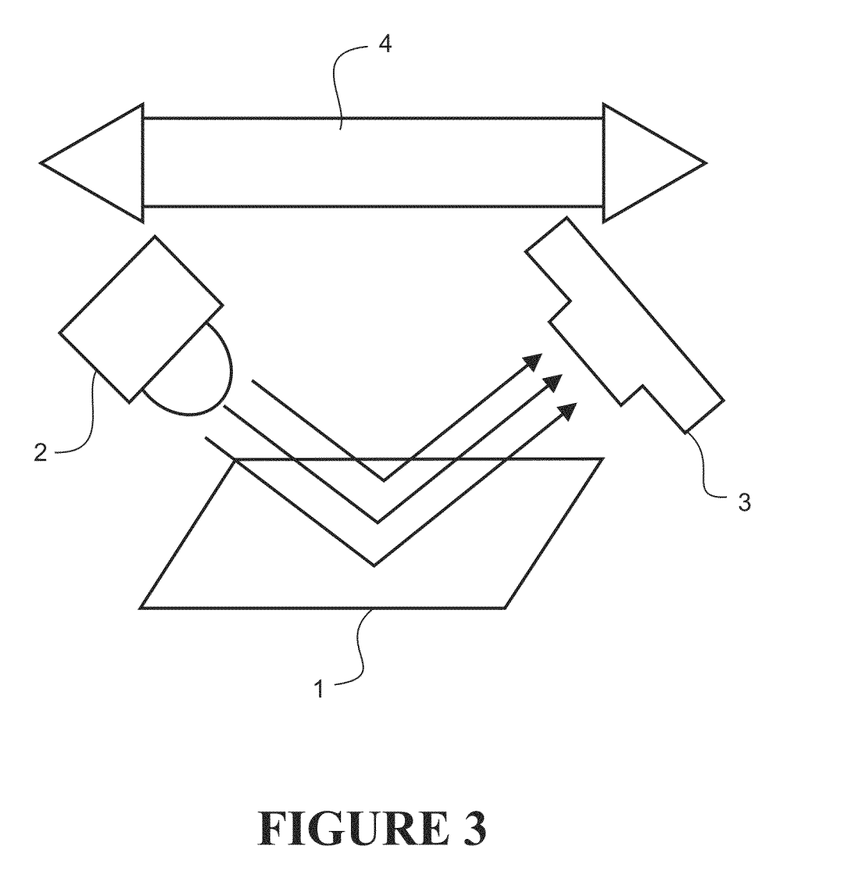
FIG. 3: is a schematic of an embodiment of a detector in accordance with the invention.

FIG. 3 illustrates one embodiment of a detector in accordance with the invention. The Figure illustrates the sample 1, which may be a dry or wet sample, a broad band UV lamp 2 as the UV source (e.g. a 325 nm source) and a diode detector 3. A germicidal lamp 4 is used as the 200-300 nm light source. The sample is placed on a flat surface and the light from 325 nm lamp is incident upon the sample. The amount of light that reflects from the sample is measured with a diode detector. The sample is then irradiated for a few minutes with the germicidal lamp. After this irradiation, the reflectance of the 325 nm lamp is measured a second time. If the sample contains spores, the amount of reflected light will decrease.

Figure 4:
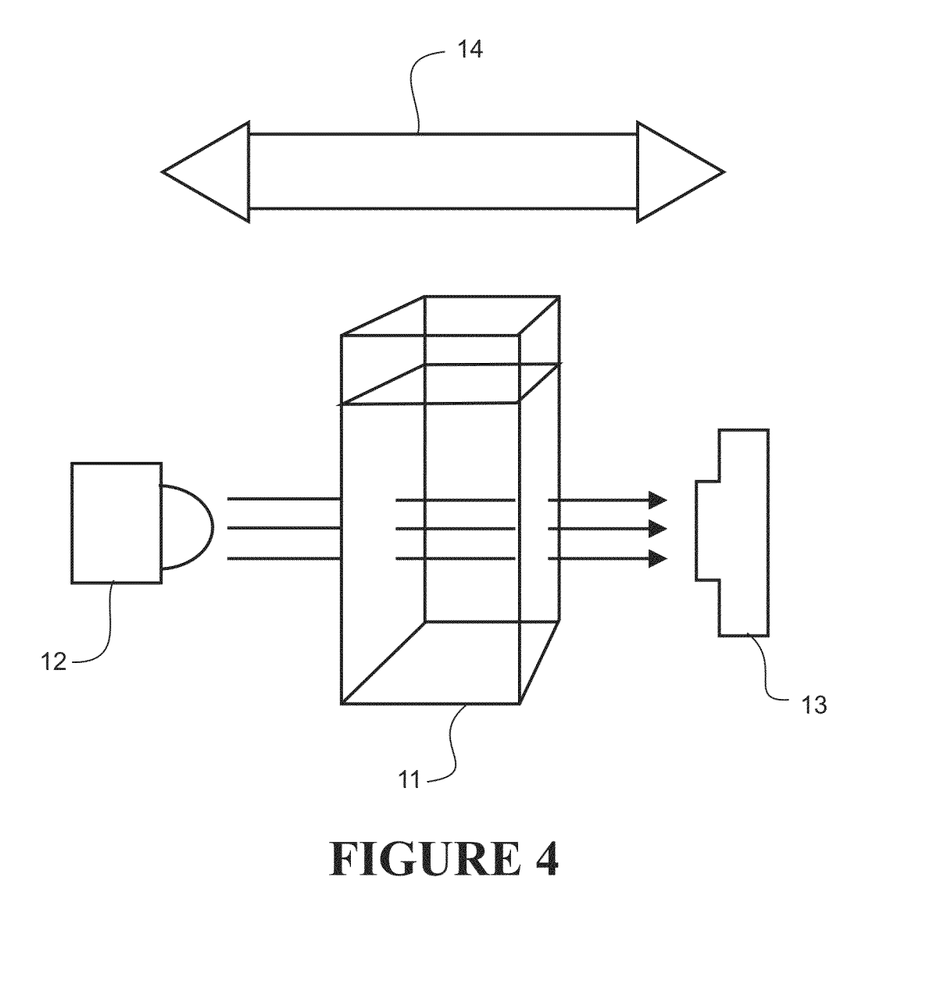
FIG. 4: is a schematic of another embodiment of a detector in accordance with the invention.

FIG. 4 illustrates another embodiment of a detector and method of the invention. The Figure illustrates the sample 11 which comprises spores in a water suspension, a UV source 12 (e.g. a 325 nm source), a diode detector 13, and a germicidal lamp (e.g. a 254 nm source) 14. The 325 nm light passes through the water suspension with the spores. The amount of light to be transmitted through the sample is measured with the photodiode. The sample is irradiated with the germicidal lamp for several minutes. Then the amount of 325 nm light to be transmitted through the sample is measured a second time. If the sample contains spores, the amount of light transmitted will decrease.

Figure 5:
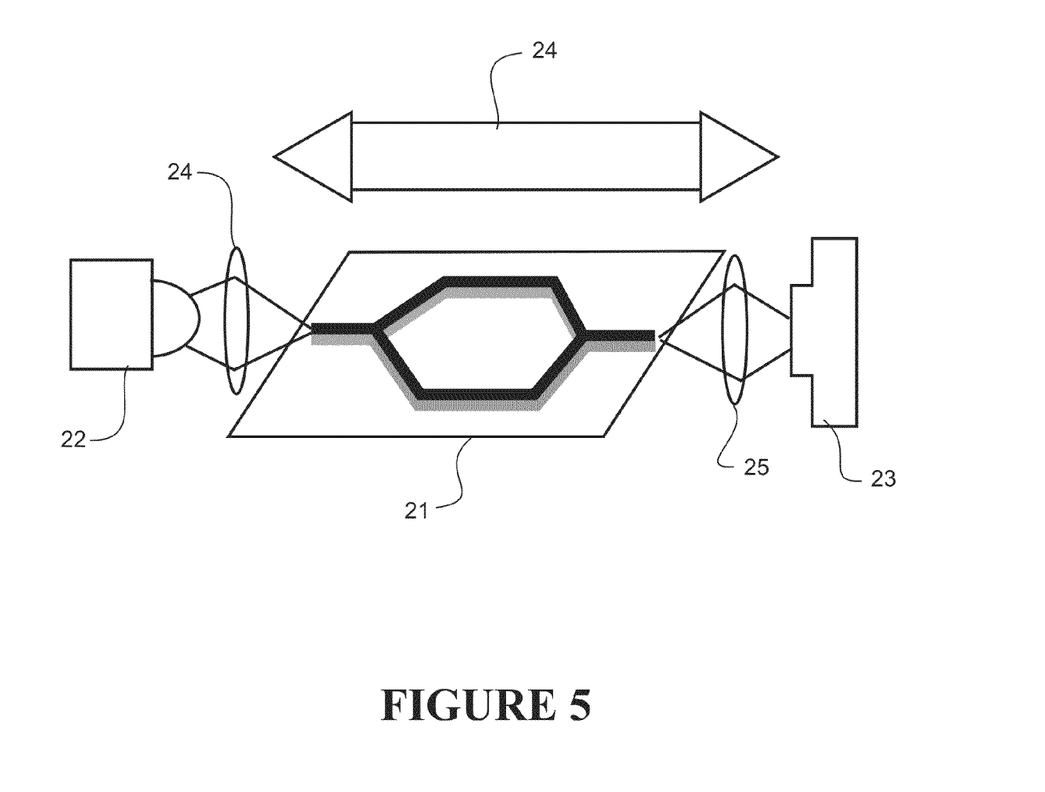
FIG. 5: is a schematic of another embodiment of a detector in accordance with the invention.
Figure 6:
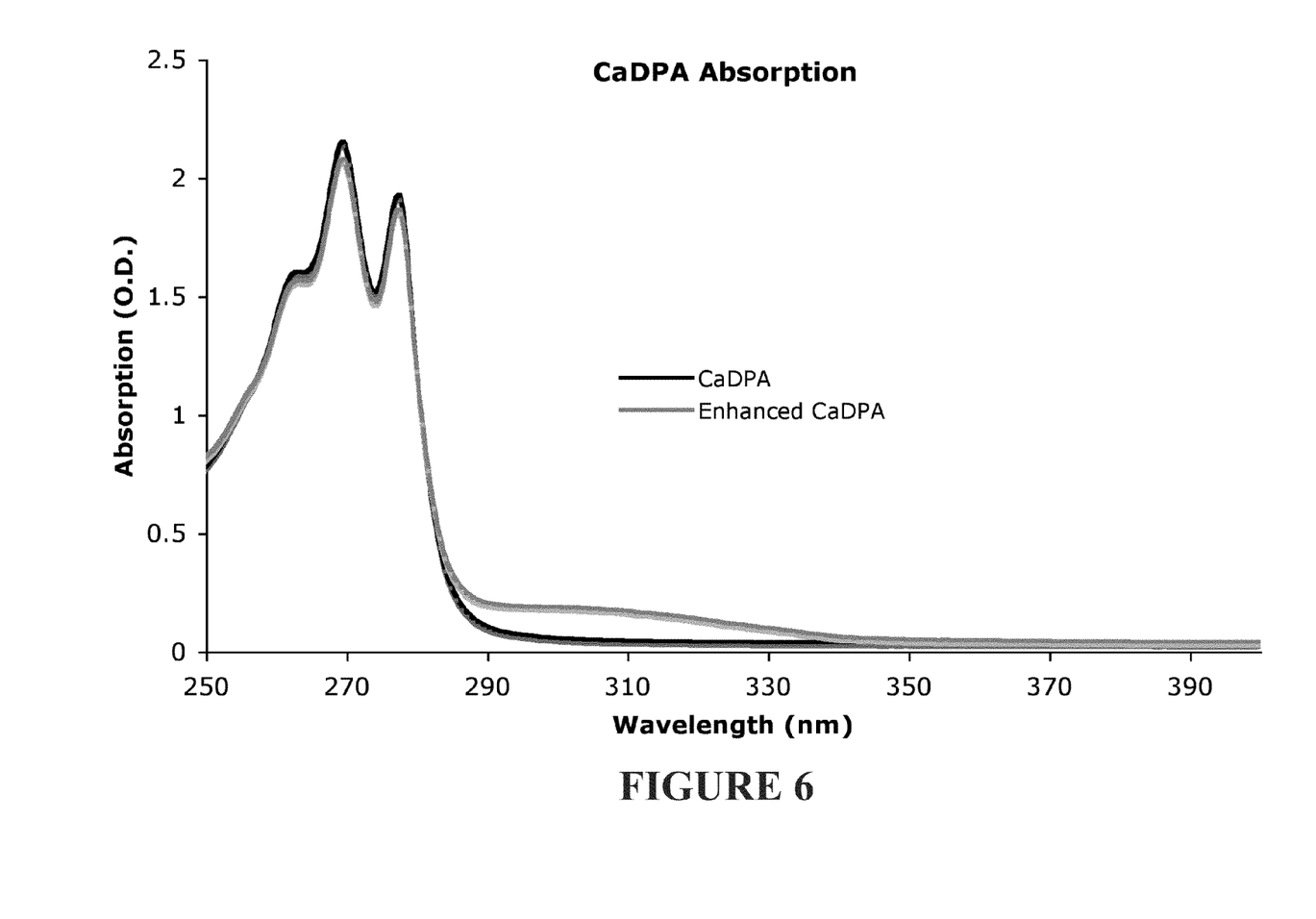
FIG. 6: is a plot of intensity against wavelength of absorption before and after irradiation with UV radiation as discussed in Example 1.
Figure 7:
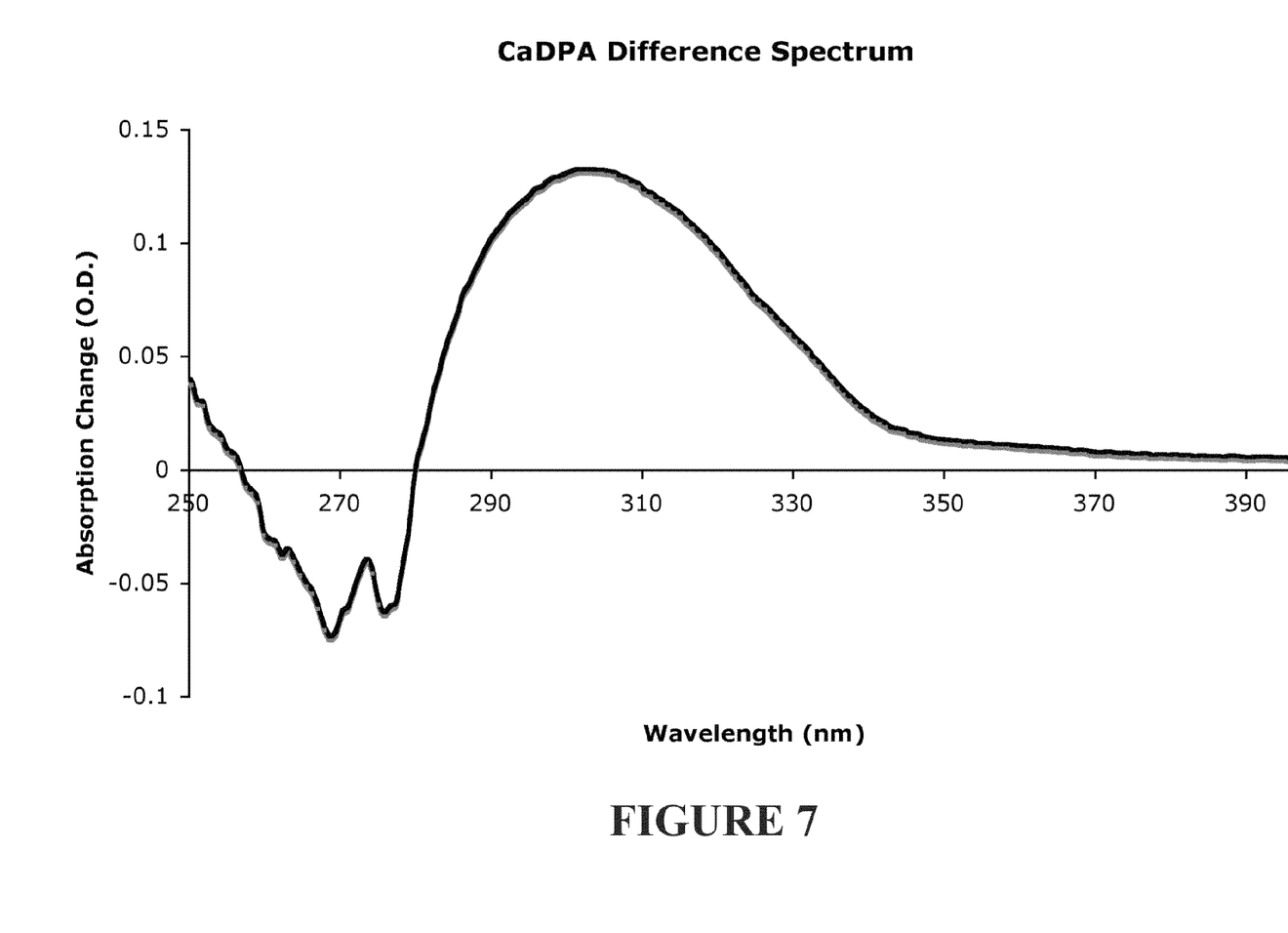
FIG. 7: is a plot of absorption change against wavelength before and after irradiation with UV radiation as discussed in Example 1.
Figure 8:
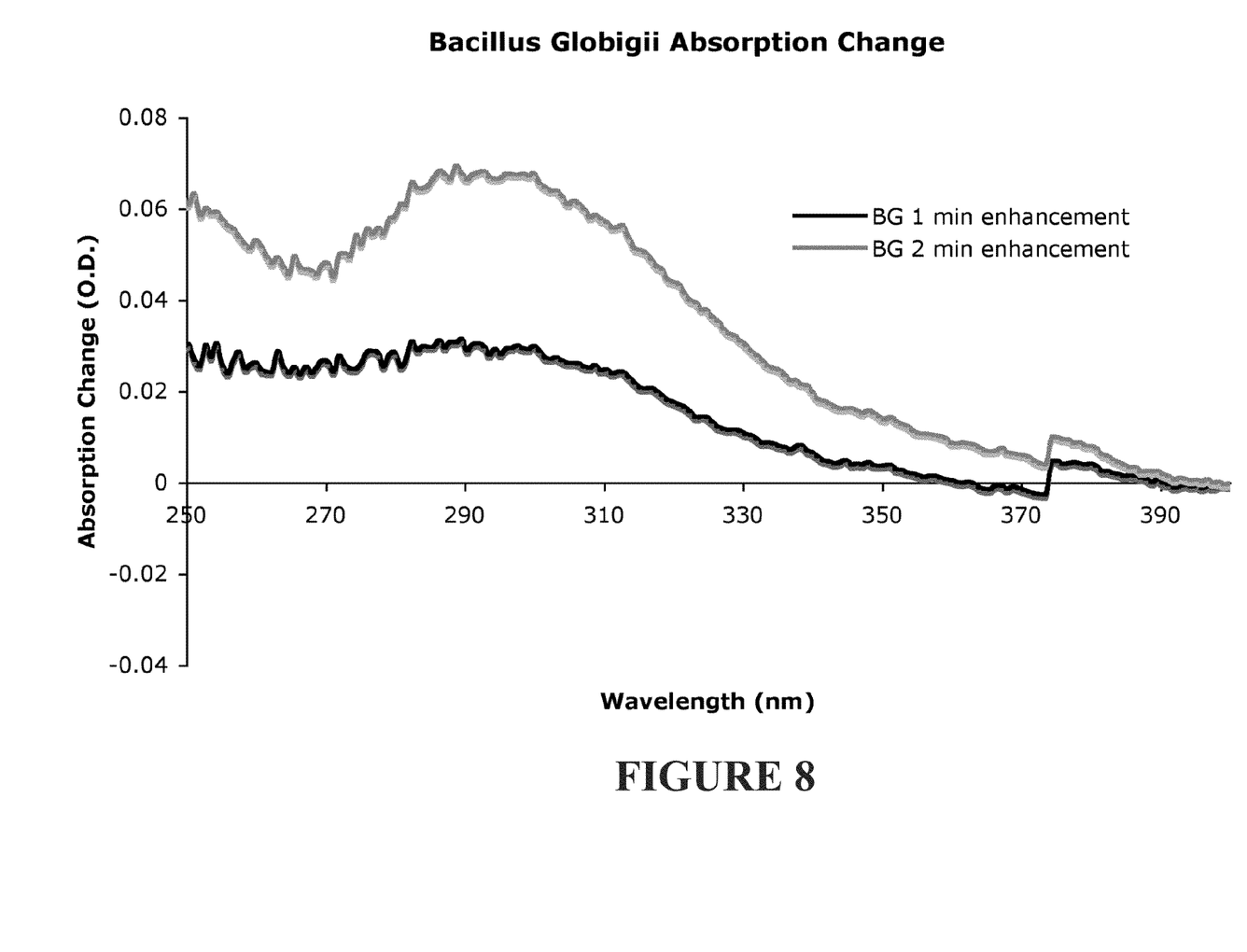
FIG. 8: is a plot of absorption change against wavelength before and after irradiation with UV radiation as discussed in Example 2.
Figure 9:
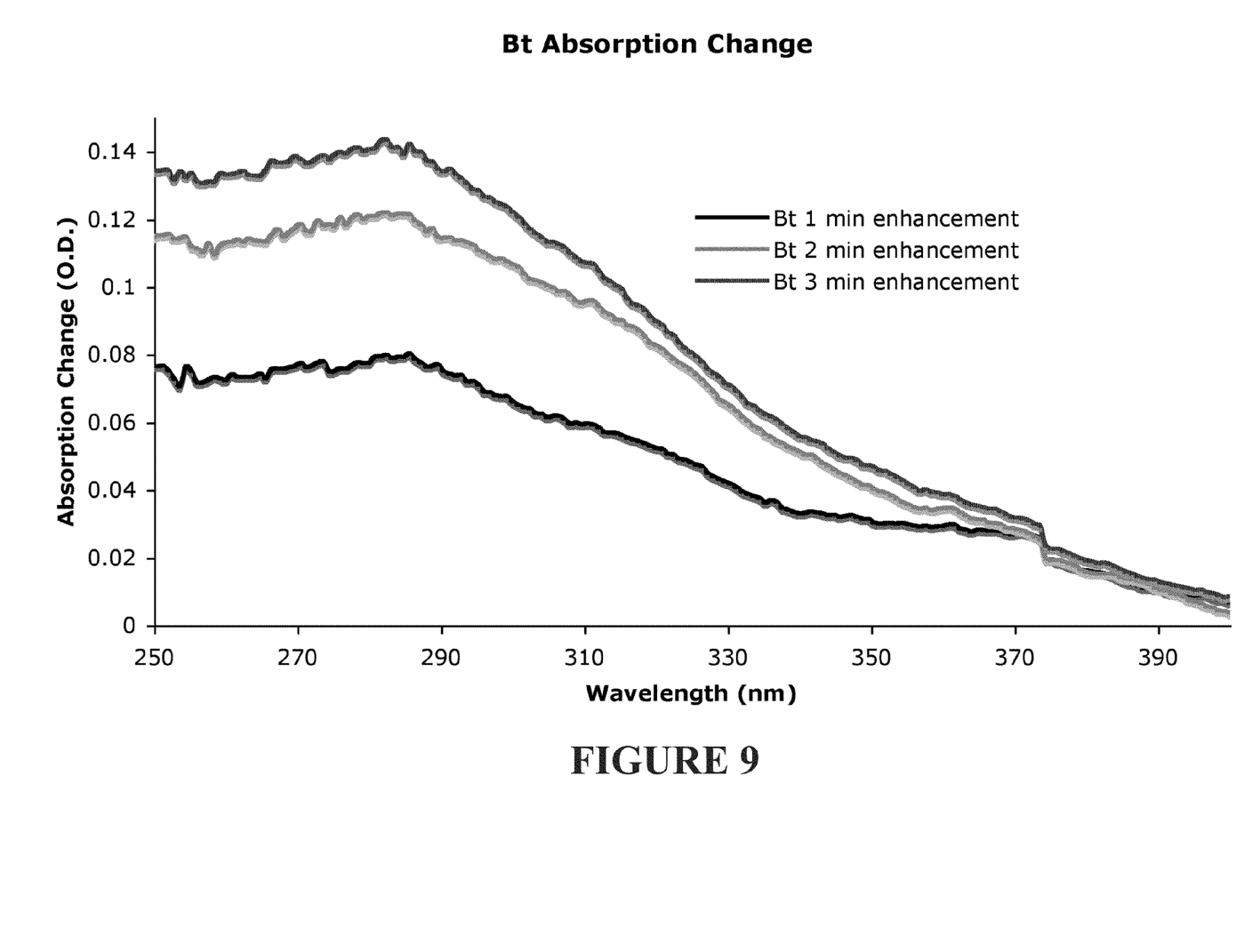
FIG. 9: is a plot of absorption change against wavelength before and after irradiation with UV radiation as discussed in Example 3.
Figure 10:
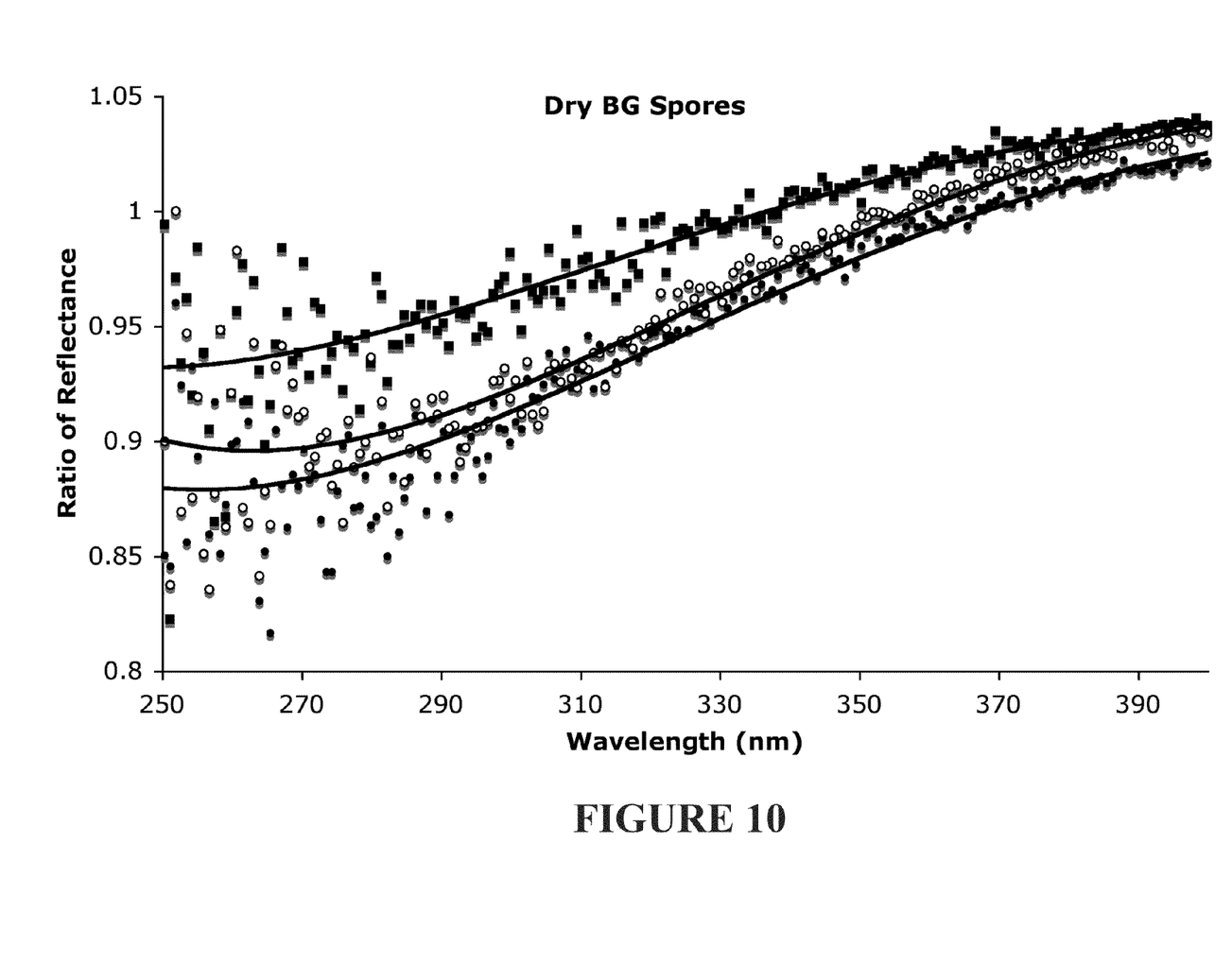
FIG. 10: is a plot of the ratio of reflectance against wavelength before and after irradiation with UV radiation as discussed in Example 4.

FIG. 5 illustrates another form of a detector and method of the invention. The Figure illustrates at 21 the waveguide interferometer such as a Mach-Zehner interferometer, a UV source 22 such as a 325 nm source, a lens 24 which focuses radiation from the source 22 onto the waveguide interferometer 21, and a lens 25 which focuses to a detector 23 The sample is placed on the waveguide interferometer so that the sample is in contact with the waveguides. The amount of light transmitted through the interferometer is measured. Then the germicidal lamp 24 is turned on and irradiates only one arm of the interferometer. While the arm is irradiated with the germicidal lamp, the transmission of the interferometer is measured. If spores are present in the sample, the optical pathlength of the irradiated arm of the interferometer will be effectively longer, thus changing the balance of light through the interferometer and changing the transmitted intensity.

UV light sources include lamps (including fluorescent lamps, gas lamps, tungsten filament lamps, quartz lamps, halogen lamps, arc lamps, and pulsed discharge lamps, for example), and UV light emitting diodes, laser diodes, laser of any type capable of producing UV radiation (such as gas, dye or solid state) and two-photon techniques where two separate photons of differing wavelength as used to provide the required excitation wavelength. For example, a 280 nm light necessary to bring about absorption, reflectance, and/or IOR changes can be achieved from a high intensity of 560 nm light. Two photons of 560 nm could be simultaneously absorbed to create the same effect and response as one 280 nm photon being absorbed. An advantage of such a two-photon absorption is that all optics and the light emitter work in the visible region of the spectrum, whilst the absorption band of the sample is in the UV region. It should be appreciated that when we refer to subjecting the sample to UV radiation, scenarios such as this are included. It is the absorption band which should be considered in this case.

Other than with the two-photon method, the bandwidth of the exciting light does not have to be very narrow. Thus some of the light sources discussed above may not need any filtering, or they could simply be filtered by gratings, interference filters or coloured glass filters. They could also be filtered by cut-off filters.

The detector may be any photodetectors for the detection of light. These may include, but are not limited to, photodiodes, phototransisitors, photoresistors, photomultipliers, pyroelectric detectors, and chemical detectors, such as photographic plates. The detector can be a single element detector like a photodiode that measures all light incident on the detector window, or it could be a image detector, like a silver halide emulsion on a photographic plate or a CCD photodiode array.

The detector needs to be sensitive to the range of wavelengths of light used to measure the absorption, reflectance, or IOR of the sample.

A detection system of the invention may include means for analysis of the absorption, reflectance, and/or IOR. Such means may include computer processing apparatus which, for example records the absorption, reflection and/or IOR recorded or detected before irradiation and compares it with that recorded or detected after, identifies any absorption, reflectance, and/or IOR changes indicating the presence of spores. The analysis means may determine actual absorption, reflectance, and/or IOR measurements or it may simply determine the difference between the first and subsequent recording, and determine if a change has been observed. The analysis means may record and store the outputs or it may simply trigger an alarm for example, if bacterial spores (or spores greater than a threshold limit) are detected.

The changes in the absorption, reflectance, and/or IOR observed in the methods of all embodiments of the invention is always due to the existence of DPA. However, the wavelengths at which changes are detected may be different depending upon the environment of the DPA. Thus in one embodiment of the invention a simple detector may be used to observe only qualitative changes and thus indicate whether or not spores are present. In an alternative embodiment, using a more specialised detector which resolves the intensity of emission as a function of wavelength, the shape of the changes in absorption, reflectance and/or IOR can be analysed to determine what class of bacterial spores are present in a sample.

The sensitivity of the detector can be set to ignore the few bacterial spores that occur naturally. Biological weaponry such as anthrax requires approximately 10,000 anthrax spores to lethally infect a person with a 50% probability. Thus the detection limit may be set at for example 100 spores. This is well above the background level for spores, and 100 times lower than the level needed to lethally infect individuals. Although many bacterial spores are relative harmless to humans, others cause gastrointestinal problems and others (like anthrax) are deadly. The levels of bacterial spores should almost always be quite low in the environment thus the detection of bacterial spores above a given threshold level would more than likely signal bioterrorism.

The invention has importance in the bioterrorism field however there are many other applications as would be known to one skilled in the art. Examples include (but are not limited to) the situation in New Zealand where the Ministry of Agriculture and Fisheries (MAF) has sprayed certain areas with *Bacillus* bacterial spores as an insecticide against unwanted pests. The method of the invention and a detector of the invention could be employed to detect levels of exposure which would be severely detrimental to the public or such susceptible persons, or to show which regions are safe for such susceptible persons to occupy during spraying.

A further important application of the method and detector of the invention is identifying and quantifying bacterial spores in dried products such as foodstuffs. One particular application is identification and quantification of *Bacillus* bacterial spores in milk powder. Milk powder providers, even with their best precautions, may still have contamination by bacterial spores in their product. Regulatory authorities set guidelines as to what is a minimum spore level for safe use and consumption by the public. Different thresholds will be appropriate for different end uses of the powder. Thus a convenient method of determining whether or not there is a spore presence and what level of presence would be advantageous. The method of the invention is suitable for such an application.

The method of the invention may also be used for detecting spores in a water supply or an air supply, in various medical applications, and in fuels, for example.

The method helps to separate the bacterial spore absorption, reflectance, and/or IOR from the absorption, reflectance, and/or IOR of other materials for example those found in dust. Thus this enhances discrimination to a point of nearly eliminating false positives.

It is also worthy of note that it may be possible to detect single spores. For example it is common to frequency double, triple and quadruple the light from a Nd:YAG laser. With use of the tripled (355 nm) and the quadrupled (266 nm) light from a Nd:YAG laser, the resolution is such that single spores may be detected by the method of the invention. Lasers other than the Nd:YAG could also be used, such as diode lasers.

The following Experimental Examples illustrate application of the invention to samples in various phases. With reference to the accompanying Figures, it is clear that absorption, reflectance, and/or IOR changes occurs when spores are present.

EXPERIMENTAL

Example 1

A sample of the calcium complex of dipicolinic acid (CaDPA) was dissolved in water. The absorption spectrum of the sample in a 1 cm cuvette was measured. Then the CaDPA was exposed to 254 nm light for a short time to enhance the absorption. (A 5 minute exposure to a 30 W germicidal lamp.) The absorption spectrum was measured after the exposure. The absorption by the sample before and after the enhancement is shown in FIG. 6.

FIG. 7 shows the CaDPA spectrum subtracted from the enhanced CaDPA spectrum. It is apparent that by monitoring the absorption near 300 nm, CaDPA, a chemical unique to bacterial spores can be identified.

Example 2

The experiment above was repeated using *Bacillus globigii* (BG) spores (also known as *Bacillus atrophaeus*) in a water suspension. They were exposed to UV light as in Example 1, for one minute and two minutes. FIG. 8 shows the difference spectra (the absorption before enhancement was subtracted from the one or two minute enhanced signal).

Example 3

Experiment 2 was repeated with a different species of bacterial spores (*Bacillus thuringiensis*—Bt) in a water suspension. This time the sample was exposed to the germicidal lamps for 1 minute, 2 minutes and 3 minutes. The difference spectra are shown in FIG. 9.

Example 4

The reflectance of a small quantity of BG spores was measured. The spores were then exposed to one, two and three minutes of the germicidal lamp in total. The reflectance was measured after each exposure. FIG. 10 shows the ratio of the reflectance after enhancement divided by the reflectance before enhancement. The curved line is fitted to the data to show the trend. It can be seen that with increased exposure the reflectance decreases near 300 nm. On the graph, the squares are 1 minute of enhancement. The open circles are two minutes of total enhancement and the solid circles are three minutes of total enhancement.

Where in the foregoing description reference has been made to elements or integers having known equivalents, then such equivalents are included as if they were individually set forth.

Although the invention has been described by way of example and with reference to particular embodiments, it is to be understood that modifications and/or improvements may be made without departing from the scope or spirit of the invention.

The invention claimed is:

1. A method of detecting the presence of bacterial spores in a sample comprising non-destructively to the spores carrying out the steps of assessing the absorption, reflectance, and/or index of refraction (IOR) of the sample, subjecting the sample to UV radiation, and reassessing the absorption, reflectance, and/or index of refraction (IOR) of the sample to determine the presence or absence of spores.

2. A method as claimed in claim 1 including subjecting the sample between assessments to UV radiation in the wavelength range 200-300 nm.

3. A method as claimed in claim 1 including spectrally resolving any fluorescence observed in the assessment and reassessment steps.

4. A method as claimed in claim 1 including subjecting the sample to UV radiation for less than 5 minutes.

5. A method of detecting bacterial spores in a sample comprising the steps of providing a detector which comprises a UV source, a detection zone within which a sample is placed or passes, means for fluorescence analysis arranged to assess for the presence of spores by reference to a change in absorption, reflectance, or index of refraction (IOR) following one and then a subsequent exposure of the sample to a UV source without altering the structure of any spore, positioning the detector so that the sample is in the detection zone, analyzing the spore content of the sample, the step of analysis of the spore content including assessing the sample for absorption, reflectance, and/or index of refraction, exposing the sample to UV radiation, and then reassessing the sample for a change in absorption, reflectance, and/or index of refraction relative to that assessed in said first assessing step, a change in absorption, reflectance, and/or index of refraction at said reassessing step being indicative of the presence of spores.

6. A method as claimed in claim 5 including detecting and identifying bacterial spores useful in biological warfare.

7. A method as claimed in claim 5 including detecting bacterial contamination of a foodstuff.

8. A detector for detecting bacterial spores in a sample comprising a UV source, a detection zone within which the sample is placed or passes, means for analysis of changes in absorption, reflectance and/or index of refraction (IOR) arranged to assess for the presence of spores by reference to an increase in absorption, a decrease in reflectance, and/or a change in index refraction following an exposure of the sample to a UV source.

9. A detector as claimed in claim 8 arranged to subject the sample to UV radiation of wavelength in the range 200-300 nm.

10. A detector as claimed in claim 8 arranged to spectrally resolve any fluorescence observed in the assessment and reassessment steps.

* * * * *